United States Patent [19]

Witt et al.

[11] Patent Number: 5,800,357
[45] Date of Patent: Sep. 1, 1998

[54] ULTRASOUND DOPPLER POWER IMAGING SYSTEM FOR DISTINGUISHING TISSUE BLOOD FLOW FROM CHAMBER BLOOD FLOW

[75] Inventors: Jerome F. Witt, Andover; Patrick G. Rafter, Woburn, both of Mass.

[73] Assignee: Hewlett-Packard Company, Palo Alto, Calif.

[21] Appl. No.: 773,676

[22] Filed: Dec. 24, 1996

[51] Int. Cl.⁶ .................................................. A61B 08/06
[52] U.S. Cl. .................................................. 600/455
[58] Field of Search .................. 128/661.07–661.1, 128/916; 600/453–456

[56] References Cited

U.S. PATENT DOCUMENTS

| | | | |
|---|---|---|---|
| 5,190,044 | 3/1993 | Kawasaki et al. | 128/661.09 |
| 5,211,169 | 5/1993 | Freeland | 128/661.1 X |
| 5,471,990 | 12/1995 | Thirsk | 128/661.09 |

*Primary Examiner*—Francis Jaworski

[57] ABSTRACT

An ultrasound imaging system enables discrimination between heart chamber blood flow and blood flow in a heart wall and includes a transducer for transmitting ultrasound pulses into a patient and for receiving ultrasound echoes from blood flow targets within the patient. A beam former/buffer converts the received ultrasound echoes into echo data patterns from which a relative velocity of a blood flow target within said patient is determinable. A strong filter preferentially enables passage of echo data pattern signals which represent a velocity that is higher than a velocity of echo pattern data signals from cardiac wall blood flow targets in the patient. A weak filter partially inhibiting echo signals from low velocity tissue targets. A selection circuit is responsive to outputs from the weak filter circuit and is further responsive to control signals from the strong filter circuit that indicate echo pattern data signals that exceed a threshold, to convert to a reference value. echo signals from the weak filter circuit which positionally correspond to targets which produce the echo data pattern signals that exceed the threshold.

10 Claims, 2 Drawing Sheets

ULTRASOUND DOPPLER POWER IMAGING SYSTEM FOR DISTINGUISHING TISSUE BLOOD FLOW FROM CHAMBER BLOOD FLOW

FIELD OF THE INVENTION

This invention relates to improvements in ultrasonic diagnostic imaging and, more particularly, to an improved method and apparatus for distinguishing blood flow in the cardiac wall from blood flow in the cardiac chamber.

BACKGROUND OF THE INVENTION

Recently, diagnostic imaging systems have become available which provide indications of flow conditions within the body by a modality known as "color Doppler velocity imaging". This technique involves the acquisition of Doppler data at different locations, called sample volumes, over the image plane of an ultrasonic image. The Doppler data is acquired over time and is used to estimate the phase shift over succeeding transmit events, at each discrete sample volume. The phase shift relates to the velocity of fluid flow in vessels within the body, with the polarity of the shift indicating direction of flow. This information is color coded in accordance with the magnitude of the shift (i.e., its velocity) and its polarity and is then overlaid on a structural image of the image plane. The colors in the image provide an indication of the speed of blood flow and its direction.

Recently, a different form of Doppler display has come into use and is referred to as color power Doppler (see U.S. Pat. No. 5,471,990 to Thirsk). This technique focuses on the intensity of received signals which exhibit a Doppler shift. The Doppler signal intensity is computed for each sample volume in an image plane and is displayed, using a color derived from a color map.

Unlike color Doppler velocity imaging, color power Doppler imaging does not exhibit the problems of direction determination, aliasing and low sensitivity (which are characteristic of velocity imaging). Color power Doppler simply displays the Doppler signal intensity at a sample volume in a coded color.

Color power Doppler displays find use where it is desirable to assess blood perfusion in an organ or structure in the body. However, when used to assess cardiac wall blood flow, it has been found difficult to distinguish cardiac wall blood flow from the blood flow within the heart chambers. More specifically, improved imaging procedures now enable injection of contrast agents which include microscopic bubbles that provide good ultrasound return signals. These contrast agents enable a bright imaging of the blood flow, both in the heart chambers and in the heart wall. Theoretically, such contrast agents should enable excellent differential imaging of the cardiac wall blood flow where, in the case of a myocardial infarct, lessened heart muscle blood flow should readily be distinguishable from chamber blood flow. However, the brightness levels from the chamber blood flow are sufficiently high that the cardiac wall blood flow is difficult to distinguish, even in the case of an infarct.

Accordingly, there is a need for an ultrasound imaging system and method which enables ready differentiation between cardiac wall blood flow and cardiac chamber blood flow.

SUMMARY OF THE INVENTION

An ultrasound imaging system enables discrimination between heart chamber blood flow and blood flow in a heart wall and includes a transducer for transmitting ultrasound pulses into a patient and for receiving ultrasound echoes from blood flow targets within the patient. A beam former/buffer converts the received ultrasound echoes into echo data patterns from which a relative velocity of a blood flow target within said patient is determinable. A strong filter preferentially enables passage of echo data pattern signals which represent a velocity that is higher than a velocity of echo pattern data signals from cardiac wall blood flow targets in the patient. A weak filter partially inhibiting echo signals from low velocity tissue targets. A selection circuit is responsive to outputs from the weak filter circuit and is further responsive to control signals from the strong filter circuit that indicate echo pattern data signals that exceed a threshold, to convert to a reference value, echo signals from the weak filter circuit which positionally correspond to targets which produce the echo data pattern signals that exceed the threshold.

DESCRIPTION OF THE DRAWINGS

FIG. 3 is a plot of magnitude versus velocity, illustrating filter characteristics of the weak wall filter and strong wall filter shown in FIG. 2.

DETAILED DESCRIPTION OF THE INVENTION

Figure 1:
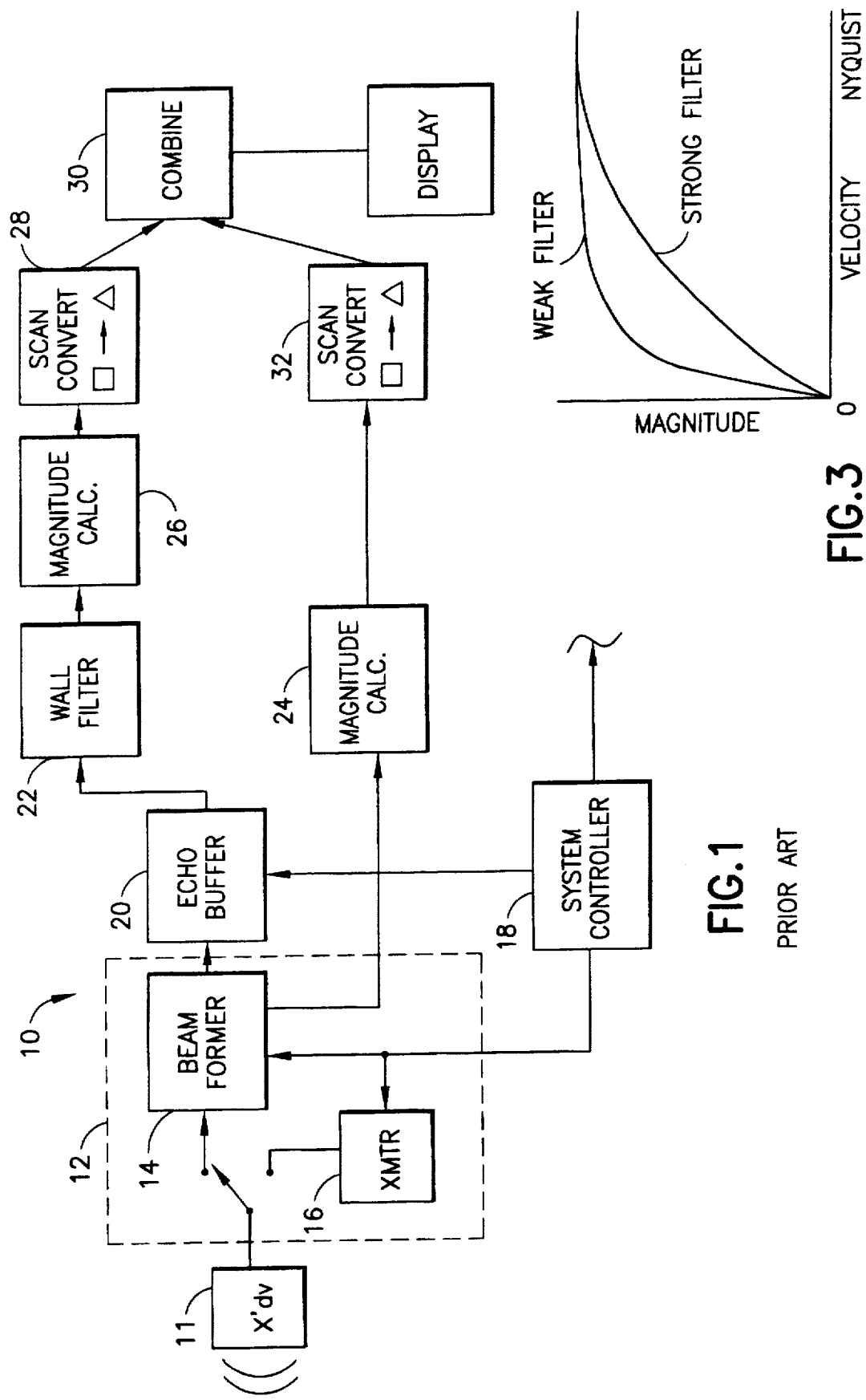
FIG. 1 is a block diagram of a prior art color Doppler display system.

Referring first to FIG. 1, prior art ultrasonic imaging system 10 includes a multi-element ultrasonic transducer 11 which transmits pulses of ultrasonic energy into the patient's body and receives ultrasonic echoes returning from structures, such as vessels, in the body. In the case of ultrasonic transmission for Doppler interrogation, it is echoes returning from moving targets (e.g. blood) that are of principal interest.

Ultrasonic transducer 11 is connected to a transmitter-receiver module 12 which includes, in the receive path, a beam former module 14 and, in the transmit path, a transmit module 16. A system controller 18 provides overall control functions for imaging system 10. After each transmit event, beam former module 14 receives echo signals that have been digitized (by means not shown), and appropriately delayed and summed to form a coherent echo signal pattern. Each echo pattern exhibits N data points (e.g., 500).

Succeeding digitized echo patterns are stored in an echo buffer 20. Thereafter, under control of system controller 18, a "slice" of data values from a given depth are accessed from the succeeding echo patterns in echo buffer 20. More specifically (and for example) a depth value (e.g. data point 250) is selected from each of the scan patterns in echo buffer 20. Recall that each scan pattern represents an image acquired at a succeeding point in time so that the slice represents successive echoes from a sample volume over a determined period of time. Any phase shift in the values of the slice data is representative of the movement of the sample volume.

The slice of data is output from echo buffer 20 and is fed to a wall filter 22. Wall filter 22 alters the digital values of the slice by removing low frequency artifacts stemming from movements of vessel walls. The filtered outputs are fed to a magnitude calculation module 26 which maps the magnitude of each filtered, digital value to a color. Those color values are then fed to a scan conversion module 28, where the scan is converted to a pie-shaped scan that is output to a combine module 30.

The echo pattern outputs from beam former 14 are also fed to a magnitude calculation module 24 which calculates the magnitudes of the unfiltered echo pattern data and outputs digital values which are, in turn, fed to a second scan conversion module 32. The outputs of scan conversion module 32 are grey scale image values of the standard ultrasound image type.

Within combine module 30, the color values from magnitude calculation module 26 are combined with the grey scale data from magnitude calculation module 24 to provide a color overlay for the grey scale data. The color data is indicative of areas of tissue that are moving above a velocity determined by wall filter 22. The combined image planes are then fed to a display wherein the pie-shaped scan is displayed.

As indicated above, when imaging both cardiac chambers and cardiac walls, the colors which result from imaging of chamber flow, especially when contrast agents have been added to the blood, tend to obscure the data from cardiac wall blood flow. It will be recalled that the operation of wall filter 28 acts to prevent low frequency artifacts from passing into magnitude calculation module 26. Therefore, what results is an output that includes digital values indicative of only targets that are moving at a velocity above a threshold, established by wall filter 28. If blood flow is occluded in the cardiac wall structure, it is difficult to visualize the occlusion, due to the high color values that are immediately adjacent as a result of the heart chamber blood velocity data.

Figure 2:
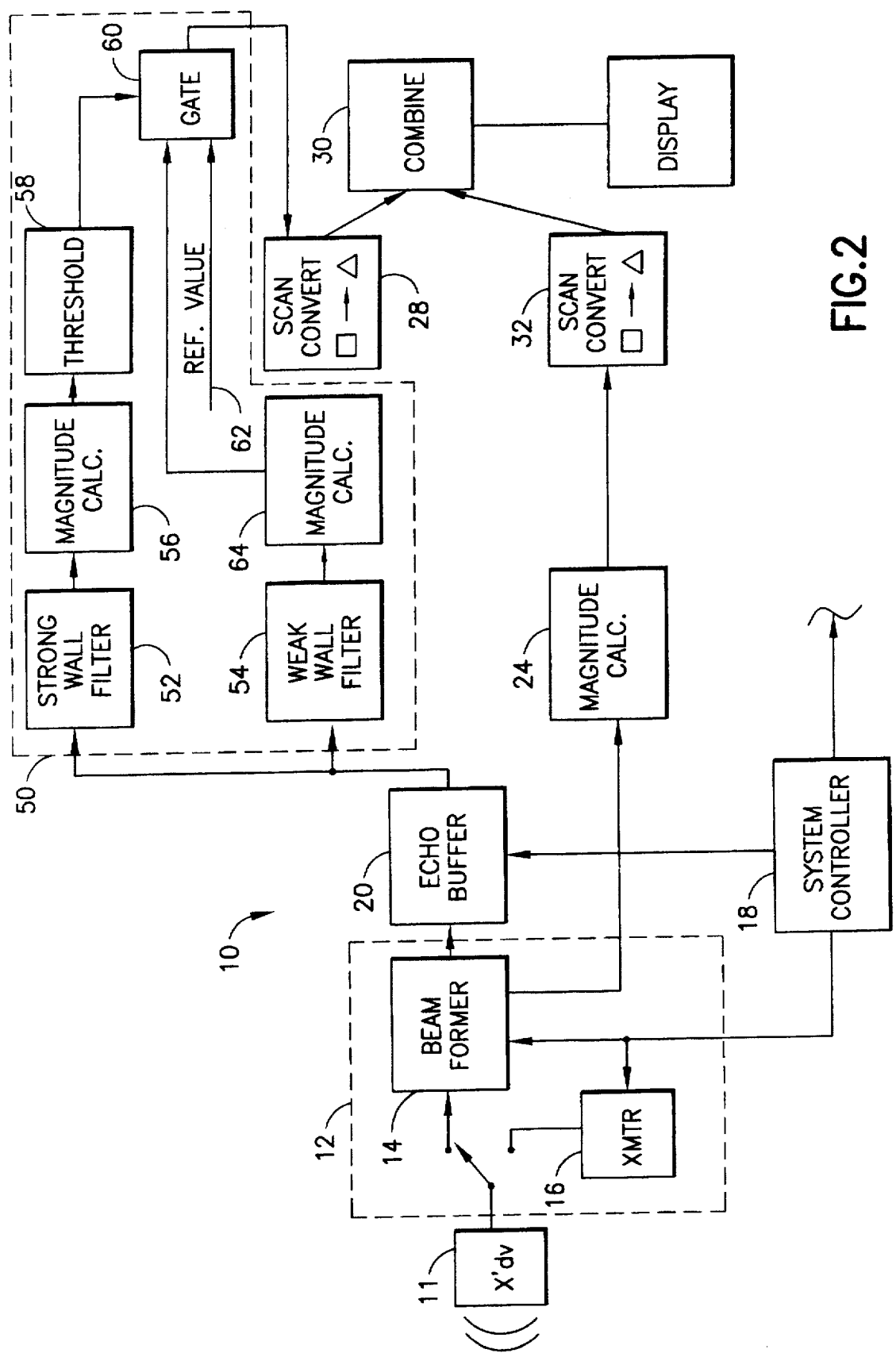
FIG. 2 is a block diagram of a color power Doppler display system incorporating the invention hereof.

Turning to FIG. 2, the prior art system of FIG. 1 has been modified in accordance with the invention, as shown within box 50. Otherwise, system 10 of FIG. 2 remains essentially similar to that shown in FIG. 1, with like reference numerals being utilized in both figures for common modules present in both. The filter system shown in FIG. 2 prevents the high brightness echoes of blood flow within the cardiac chambers from obscuring lower brightness blood flow echoes from flow paths in the cardiac walls.

More specifically, wall filter 22 of FIG. 1 has been replaced by two filters, i. e., a "strong" wall filter 52 and a "weak" wall filter 54. Strong wall filter 52 is set up to enhance the magnitude of echo signals (in a slice) which manifest larger phase shift characteristics and are thus indicative of higher velocity targets (i.e., those which are present in the high velocity blood flow within cardiac chambers). Strong wall filter 52 is thus provided with a characteristic (see FIG. 3) which enables velocities to be discriminated due to the sloped relationship between velocity and magnitude.

By contrast, the output of weak wall filter 54 enables both the lower velocity and higher velocity echo signals to pass, but provides some filter action with respect to very slow velocity targets. More specifically, only signals manifesting a small phase shift have their magnitudes decreased by the filter action of weak wall filter 54.

The digital data outputs from strong wall filter 52 are applied to a magnitude calculation module 56 which provides digital magnitude outputs for the data values. Such digital magnitudes are fed to a threshold module 58 which determines if each particular digital magnitude value from magnitude module 56 exceeds a preset threshold. If the threshold is exceeded, a switching signal is fed to gate 60.

The two inputs to gate 60 are (i) a reference value applied via line 62 and (ii) digital values, calculated by magnitude calculation module 64 which are indicative of the magnitudes of filtered echo signals from weak wall filter 54. Recall, the output of magnitude calculation module 64 is indicative of velocity echo signals from both the cardiac wall and the cardiac chamber.

When the output from threshold module 58 indicates that a chamber velocity echo signal exceeds the threshold, the corresponding control signal applied to gate 60 enables passage of the reference value into scan conversion module 28, in lieu of the corresponding filtered output value from magnitude calculation module 64. At any other time, the control output from threshold module 58 enables passage of the filtered magnitude values from weak wall filter 54. The result of this action is that the returns from the chamber which manifest a larger phase shift act as a gating function to enable substitution therefor of a reference value. That reference value is chosen so that a color assigned thereto provides high contrast to the adjacent, lower velocity, echo returns from blood flow in the heart wall.

As a result of the above-described action, for any image volume, the corresponding echo signal passed to scan convert module 28 is either the value of the actual return, as output from weak wall filter 54, or a reference value. The operation of the system of FIG. 2 thus enables the removal of the high velocity flow echo signals and their replacement by a reference value whose eventual color provides high contrast to the lower velocity wall flow signals. Thereafter, the signals are passed through combine module 28 and are displayed, as described for FIG. 1.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. An ultrasound imaging system for enabling discrimination between heart chamber blood flow and blood flow in a heart wall, said system comprising:

transducer means for transmitting ultrasound pulses into a patient and for receiving ultrasound echoes of said pulses from blood flow targets within said patient;

beam means for converting received ultrasound echoes into echo data patterns from which a relative velocity of a blood flow target within said patient is determinable;

strong filter means coupled to said beam means for preferentially enabling passage of echo data pattern signals which represent a velocity that is higher than a velocity of echo pattern data signals from cardiac wall blood flow targets in said patient, said velocity being a blood flow velocity which is experienced in said heart chamber;

weak filter means coupled to said beam means for partially inhibiting echo signals from low velocity tissue targets; and selection means responsive to outputs from said weak filter means and further responsive to control signals derived from said strong filter means that indicate echo pattern data signals that exceed a threshold set to discriminate signals corresponding to said velocity which is experienced in said heart chamber, to convert to a reference value, echo signals from said weak filter means which positionally correspond to targets which produce said echo data pattern signals that are discriminated by said threshold.

2. The ultrasound imaging system as recited in claim 1, further comprising:

magnitude means for converting echo signals to grey scale values;

combining means coupled to said selection means and said magnitude means for combining positionally corresponding grey scale values from said magnitude means and echo signals from said selection means, after alteration thereof by selective insertion of reference values; and means coupled to said combining means for displaying an ultrasound image derived from said grey scale values, said reference values and said echo signals from said selection means.

3. The ultrasound imaging system as recited in claim 1, wherein said strong filter means exhibits an output characteristic which alters higher velocity echo pattern data signals to enable subsequent discrimination thereof.

4. The ultrasound imaging system as recited in claim 3, wherein said strong filter means includes magnitude determination means for assigning, after filtering, a magnitude value to each echo pattern data signal value, and means for determining which echo pattern data signal values exceed said threshold value, and for providing a control signal to said selection means for each echo pattern data signal value which exceeds said threshold value, each said control signal causing said selection means to substitute said reference value for an echo pattern data signal value from said weak filter means.

5. The ultrasound imaging system as recited in claim 4, wherein said weak filter means includes magnitude determination means for assigning, after filtering, a magnitude value to each digital signal value, each said magnitude value representative of a color.

6. The ultrasound imaging system as recited in claim 4, wherein said reference value is indicative of a reference color which is readily distinguished by a viewer from a color assigned to said echo signals from cardiac wall blood flow targets.

7. An ultrasound imaging method for enabling discrimination between heart chamber blood flow and blood flow in a heart wall, said method comprising the steps of:

a) transmitting ultrasound pulses into a patient and receiving ultrasound echoes of said pulses from blood flow targets within said patient;

b) converting received ultrasound echoes into echo pattern data signals from which a velocity of a blood flow target within said patient is determinable;

c) strongly filtering said echo pattern data signals so as to enable subsequent velocity discrimination thereof;

d) generating a control signal when any echo pattern data signal exceeds a determined threshold value which is set to discriminate data patterns manifesting blood velocities experienced in said heart chamber; and e) selecting echo pattern data signals in accordance with control signals, derived from step d), that correspond to echo signals that are discriminated by said determined threshold value, so as to convert to a reference value, echo pattern data signals which positionally correspond to targets which produced said echo pattern data signals that are discriminated by said determined threshold value.

8. The ultrasound imaging method as recited in claim 7, comprising the further step of:

d1) weakly filtering said echo pattern data signals so as to partially inhibit echo signals from low velocity tissue targets, and utilizing filtered echo pattern data signals in said selecting step e).

9. The ultrasound imaging method as recited in claim 7, further comprising the steps of:

f) converting said echo signals to grey scale values;

g) combining positionally corresponding grey scale values from step f) and echo signals from step e), after alteration thereof by selective insertion of reference values; and h) displaying an ultrasound image derived from said grey scale values, said reference values and said echo signals.

10. The ultrasound imaging method as recited in claim 9, wherein said reference value is indicative of a reference color which is readily distinguished by a viewer from a color assigned to echo signals from cardiac wall blood flow targets.

* * * * *